(12) United States Patent
Ding et al.

(10) Patent No.: US 10,611,992 B2
(45) Date of Patent: Apr. 7, 2020

(54) **METHOD FOR RAPIDLY CHARACTERIZING CONTENT VARIATIONS OF TRITERPENOIDS IN LIQUID FERMENTATION PROCESS OF *ANTRODIA CAMPHORATA***

(71) Applicant: Jiangnan University, Wuxi (CN)

(72) Inventors: Zhongyang Ding, Wuxi (CN); Mengmeng Xu, Wuxi (CN); Zhenghong Xu, Wuxi (CN); Zhijian Huang, Wuxi (CN); Han Wang, Wuxi (CN); Liting Zhao, Wuxi (CN); Guiyang Shi, Wuxi (CN); Gaoqiang Liu, Wuxi (CN); Lianzhong Ai, Wuxi (CN); Zhicai Zhang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/177,575

(22) Filed: Nov. 1, 2018

(65) Prior Publication Data
US 2019/0071629 A1    Mar. 7, 2019

Related U.S. Application Data

(63) Continuation of application No. PCT/CN2017/095842, filed on Aug. 3, 2017.

(30) Foreign Application Priority Data

Jul. 27, 2017    (CN) .......................... 2017 1 0622974

(51) Int. Cl.
    *C12P 15/00* (2006.01)
    *C12M 1/34* (2006.01)
    *C12M 1/36* (2006.01)
(52) U.S. Cl.
    CPC ............ *C12M 41/34* (2013.01); *C12M 41/48* (2013.01); *C12P 15/00* (2013.01)
(58) Field of Classification Search
    None
    See application file for complete search history.

(56) References Cited

U.S. PATENT DOCUMENTS

| 2016/0348063 A1 | 12/2016 | Chen et al. |
| 2017/0159008 A1 | 6/2017 | Chuang et al. |

FOREIGN PATENT DOCUMENTS

| CN | 106434821 A | 2/2017 |
| CN | 106883010 A | 6/2017 |
| WO | 2015024190 A1 | 2/2015 |

OTHER PUBLICATIONS

Zhen-Ming Lu et al. "Alpha-terpineol promotes triterpenoid production of Antrodia cinnamomea in submerged culture". FEMS Microbiol Lett 2014, 358, pp. 36-43.*
Chen et al. "Study on volatile components in Antrodia camphorate powder and their fingerprints analysis by HSGC/MS". Zhipu Xuebao (2014), 35(2), 149-157.*
Zhen-Ming Lu et al. "Analysis of volatile compounds of Antrodia camphorata in submerged culture using headspace solid-phase microextraction". Food Chemistry 2011, 127, pp. 662-668.*
Xu, Mengmeng. Analysis of volatile compounds of antrodia camphorate during submerged fermentation. Food Science. Apr. 26, 2017, 38(34) 159-164.

* cited by examiner

*Primary Examiner* — Vera Afremova
(74) *Attorney, Agent, or Firm* — IPro, PLLC

(57) ABSTRACT

The present invention discloses a method for rapidly characterizing content variations of triterpenoids in a liquid fermentation process of *Antrodia camphorata*, belonging to the field of microbial fermentation. According to the method of the present invention, in the liquid fermentation of *Antrodia camphorata*, an analysis method of rapidly judging the content variations of triterpenoids by rapid on-line or off-line detection and analysis of the content of a volatile aromatic substance α-terpineol is utilized to implement automatic control of the fermentation process. Predictive analysis of triterpenoids in the fermentation process based on variations in on-line real-time parameters increases the controllability and production predictability of the fermentation process. This is of great significance for the development and utilization of *Antrodia camphorata* products having various bioactivities and application thereof in industrial production.

13 Claims, 12 Drawing Sheets

METHOD FOR RAPIDLY CHARACTERIZING CONTENT VARIATIONS OF TRITERPENOIDS IN LIQUID FERMENTATION PROCESS OF *ANTRODIA CAMPHORATA*

TECHNICAL FIELD

The present invention relates to a method for rapidly characterizing content variations of triterpenoids in a liquid fermentation process of *Antrodia camphorata*, belonging to the field of microbial fermentation.

BACKGROUND

*Antrodia camphorata* is perennial basidiomycetes belonging to family Polyporales of order Aphyllophorales in class Basidiomycetes, grows only in *Cinnamomum kanehirae* in Taiwan, and is a rare edible and medicinal fungus. Its mycelium and fruiting bodies have many physiological activities, such as liver protection, anti-oxidation and anti-inflammation. Polysaccharides, terpenoids and steroids are the main active compounds of *Antrodia camphorata*. Triterpenoids are one of the most important active substances. They are natural compounds composed of isoprene as a constitutional unit, which are connected end to end after removal of the hydroxyl group. Pharmacological studies have shown that the triterpenoids of *Antrodia camphorata* have multiple biological activities, such as liver protection, immunoregulation, anti-inflammation, anti-oxidation, blood pressure lowering, etc., and have a good therapeutic effect on tumors and cancers. *Antrodia camphorata* existing in nature grows on *Cinnamomum kanehirae*, grows very slowly, is sparsely populated, and is expensive.

Traditional edible and medicinal fungi are often cultured in a solid cultivation mode, and their growth environment conditions are close to the natural state, but the solid cultivation has the defects of long culture period and unstable metabolite bioactivities and is prone to microbiological contamination. Compared with traditional solid cultivation, the characteristics of short period and easy scale-up of liquid fermentation are more prominent. Many fungi that are not easily succeeded by artificial solid cultivation, such as *Antrodia camphorata* and *Collybia maculata*, have also successfully achieved liquid fermentation. However, since the triterpenoids of *Antrodia camphorata* are mainly present in the mycelium (i.e., inside the cell), the determination of the triterpenoids of *Antrodia camphorata* in the fermentation process needs the steps of (1) sampling, (2) solid-liquid separation, (3) room-temperature leaching, decoction or heat reflux extraction on mycelium by using organic solvents and (4) assay determination of extracted samples, and takes a long time, and especially in the third step, it takes 3 hours or more, with obvious delay. Whether in experimental research or industrial production, this delay is very unfavorable for real-time monitoring and control of the *Antrodia camphorata* liquid fermentation process with triterpenoids as the target product. Therefore, it is urgent and necessary to establish a method for rapidly characterizing the variation trend of content of triterpenoids in the liquid fermentation process of *Antrodia camphorata*.

SUMMARY

The objective of the present invention is to provide a method for rapidly characterizing the variation trend of content of triterpenoids in a liquid fermentation process of *Antrodia camphorata*. The principle is to establish a quantitative relationship between a certain volatile substance and triterpenoids by analyzing volatile aromatic substances in the fermentation broth of *Antrodia camphorata* so that it becomes a parameter for rapid characterization of the content variations of triterpenoids in the fermentation process.

The method for rapidly characterizing the content variations of triterpenoids in the liquid fermentation process of *Antrodia camphorata* according to the present invention is to characterize the content variations of triterpenoids by rapidly determining a volatile aromatic substance α-terpineol in the fermentation process.

The α-terpineol according to the present invention is a monoterpenoid volatile aromatic substance produced in the liquid fermentation process of *Antrodia camphorata*, which is a colorless viscous liquid and has a unique clove aroma. In the fermentation process, its variation trend of content is consistent with the variation trend of content of triterpenoids, and thus, can well characterize the content variations of triterpenoids in the fermentation process.

The determination of α-terpineol according to the present invention may be assay determination by an on-line detection system of a fermentation system, or may be off-line detection.

The on-line detection device according to the present invention is to mount a process mass spectrometer, an electronic nose and other on-line detection instruments and a parameter acquisition system in an exhaust gas analysis part of a fermentor, and perform on-line detection and analysis on the α-terpineol in the fermentation process.

In an implementation of the present invention, the on-line detection device is a circulation loop formed by connecting exhaust gas generated in the fermentation process to the electronic nose through a hose. In the present invention, the electronic nose is used to monitor the concentration of α-terpineol in the exhaust gas in the fermentation process so as to calculate the amount of the α-terpineol in the fermentation broth.

In an implementation of the present invention, the detection method of the electronic nose is as follows: the detection time of the electronic nose is 100 s; the headspace temperature is 25° C.; the internal flow is 300 mL/min; and the injection flow is 300 mL/min.

In an implementation of the present invention, the off-line detection device is a headspace solid phase microextraction-gas chromatography-mass spectrometer, which periodically samples the fermentation broth of *Antrodia camphorata* and performs off-line detection and analysis on the α-terpineol in the fermentation process.

The present invention has the following advantages:

The method for detecting the content variations of triterpenoids of *Antrodia camphorata* in the fermentation process according to the present invention can make an approximately real-time rapid dynamic process preliminary determination on the fermentation process (even if the sample is taken for off-line detection, the measurement time of each sample is not more than 50 minutes), and can also be used to judge whether the fermentation is abnormal or not on such a basis, thereby implementing automatic control on the fermentation process. Predictive analysis of triterpenoids in the fermentation process based on variations in on-line real-time parameters increases the controllability and production predictability of the fermentation process. This is of great significance for the development and utilization of

*Antrodia camphorata* products having various bioactivities and application thereof in industrial production.

BRIEF DESCRIPTION OF FIGURES

FIG. 5A shows 1,2-decanediol, FIG. 5B shows linalool, FIG. 5C shows 1-octen-3-ol, FIG. 5D shows methyl furan-3-carboxylate, FIG. 5E shows 3-octanone, FIG. 5F shows phenethyl alcohol, FIG. 5G shows cubenol, FIG. 5H shows n-caprylic Octanal, FIG. 5I shows Trans-(E)-Nerolidol, FIG. 5J shows trans-2-octen-1-ol.

FIG. 6A shows 1,2-decanediol, FIG. 6B shows linalool, FIG. 6C shows 1-octen-3-ol, FIG. 6D shows methyl furan-3-carboxylate, FIG. 6E shows 3-octanone, FIG. 6F shows phenethyl alcohol, FIG. 6G shows cubenol, FIG. 6H shows n-caprylic Octanal, FIG. 6I shows Trans-(E)-Nerolidol, FIG. 6J shows trans-2-octen-1-ol.

DETAILED DESCRIPTION

Figure 1:
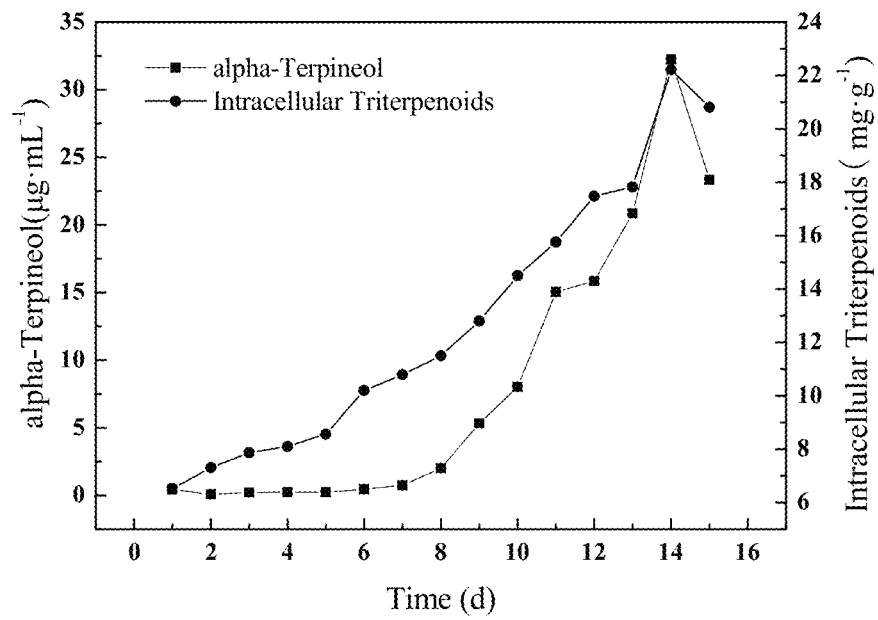
FIG. 1 shows the yields of α-terpineol and triterpenoids as a function of time in the fermentation process of Example 1.

Determination Method of Triterpenoids:

1) The mycelium obtained by centrifugation of a fermentation broth was rinsed with deionized water (washing off medium components), and freeze-dried to obtain a dried mycelium. The dried mycelium was accurately weighed 500 mg after liquid nitrogen milling, 15 mL of anhydrous ethanol was added, and the mixture was leached with 90° C. hot water for 1 h, the extraction being repeated three times. The final extraction solution was centrifuged for 10 min under a centrifugal force of 7104×g, and the volume was adjusted to 25 mL. The solution was diluted to an appropriate concentration, and 1 mL was sampled and determined according to a standard curve determination method. By using a reagent blank as a control, the absorbance was measured at 550 nm, and the content of the triterpenoids was calculated according to the standard curve.

2) Determination of oleanolic acid standard curve: 5.00 mg of oleanolic acid standard sample was accurately weighed, and dissolved in anhydrous ethanol to a 0.1 g·L$^{-1}$ solution. 0.2, 0.4, 0.6, 0.8, 1.0, 1.2, 1.4, 1.6, 1.8 and 2.0 mL were respectively put in a 25 mL colorimetric tube, evaporated to dryness in boiling water, 0.3 mL of freshly prepared 5% (mass to volume) vanillin-glacial acetic acid and 1.00 mL of perchloric acid were added, and treatment is performed in a 60° C. water bath for 20 min. After cooling, 4 mL of glacial acetic acid was added, shaken well to make it fully react. By using a reagent blank as a control, the absorbance was measured at 550 nm.

Off-line detection method of α-terpineol (headspace solid phase microextraction-gas chromatography-mass spectrometer):

1) The α-terpineol was subjected to content detection, the added internal standard being chromatographically pure n-butanol.

2) The content of the α-terpineol was calculated by an internal standard method: a certain weight of n-butanol was added as an internal standard to a certain amount of the *Antrodia camphorata* liquid fermentation broth mixture, then the sample containing n-butanol was subjected to chromatographic analysis to respectively determine the peak areas and relative correction factors of the n-butanol and the measured component, and the percentage of the measured component in the sample could be calculated according to the equation and method.

3) The headspace solid phase microextraction conditions: The extraction head was aged at the GC injection port until no impurity peak was found, and then extraction was performed at 55° C. for 30 min. The adsorbed volatile compounds were desorbed for 5 min at 250° C. at the GC injection port and flushed into the GC chromatographic column. At the same time, the instrument was started to collect data. Extraction head: DVB/CAR/PMDS.

4) Gas chromatography conditions: Chromatographic column: DB-WAX; carrier gas: helium, 1.2 mL·min$^{-1}$; temperature programmed condition: holding at 40° C. for 1 min, heating at 4° C.·min$^{-1}$ to 120° C., heating at 10° C.·min$^{-1}$ to 240° C., and holding for 6 min.

5) Mass spectrometry conditions: Interface temperature 250° C.; ionization source temperature: 250° C.; quadrupole temperature 150° C.; ionization potential: 70 eV; ionization mode: EI$^+$; mass scanning range m/z 30-450 amu.

EXAMPLE 1

(1) Culture Conditions 1

*Antrodia camphorata* strain: ATCC200183

PDA slant medium (g·L$^{-1}$): Potato 200, glucose 20, agar 20.

Seed liquid medium (g·L$^{-1}$): Bran 10, corn flour 10, glucose 20, MgSO$_4$.7H$_2$O 2, VB$_1$ 0.1, KH$_2$PO$_4$ 3.

Fermentation liquid medium (g·L$^{-1}$): Bran 10, corn flour 10, glucose 20, MgSO$_4$.7H$_2$O 2, VB$_1$ 0.1, KH$_2$PO$_4$ 3, pH 5.5.

Seed slant: The *Antrodia camphorata* strain stored at 4° C. was activated, the PDA slant medium was inoculated with the activated *Antrodia camphorata* strain, and the activated *Antrodia camphorata* strain was cultured at 28° C. for 20 days.

Primary seed liquid fermentation: The *Antrodia camphorata* strain stored at 4° C. was activated, and the liquid seed medium was inoculated with a small square of 1 cm$^2$. Each bottle was filled with 80 mL of seed medium (250 mL), and after the inoculation, culture was carried out under the conditions of 28° C. and 110 r·min$^{-1}$ for 10 days.

Secondary shake flask liquid fermentation: The well-grown primary seed liquid was mixed, 500 mL shake flasks were uniformly inoculated with the mixed well-grown primary seed liquid, the amount of each bottle being 150 mL, and the inoculum volume being 10 mL, and after the inoculation, culture was carried out under the conditions of 28° C. and 110 r·min$^{-1}$ for 15 days.

(2) Off-Line Determination of Contents of α-Terpineol and Triterpenoids

Under the culture conditions of Example 1, the variation trend of contents of the α-terpineol and triterpenoids in the fermentation process are shown in FIG. 1. The variation trends of the two are consistent. Correlation analysis and unary linear regression analysis of α-terpineol and triterpenoids with SPSS21.0 software show that the α-terpineol is positively correlated with triterpenoids in terms of content and the Pearson correlation coefficient is 0.958. Further, unary linear regression analysis was performed on the two to obtain the quantitative regression equation between the two as Y=0.460X+8.976.

In the present Example, after the *Antrodia camphorata* fermentation broth was sampled, at least 10 mL of the fermentation broth was centrifuged for 10 minutes under the centrifugal force of greater than or equal to 7104×g, then 5 mL of the supernatant was put into the headspace bottle, and the α-terpineol was determined by the headspace solid phase microextraction-gas chromatography-mass spectrometry according to the method as described in the specification.

EXAMPLE 2

(1) Culture Conditions 2
*Antrodia camphorata* strain: ATCC200183
PDA slant medium (g·L$^{-1}$): Potato 200, glucose 20, agar 20.
Seed liquid medium (g·L$^{-1}$): Bran 10, corn flour 10, glucose 20, MgSO$_4$.7H$_2$O 2, VB$_1$ 0.1, KH$_2$PO$_4$ 3.
Fermentation liquid medium (g·L$^{-1}$): Bran 10, corn flour 10, glucose 20, MgSO$_4$.7H$_2$O 2, VB$_1$ 0.1, KH$_2$PO$_4$ 3, pH 4.5.
Seed slant: The *Antrodia camphorata* strain stored at 4° C. was activated, the PDA slant medium was inoculated with the activated *Antrodia camphorata* strain, and the activated *Antrodia camphorata* strain was cultured at 28° C. for 20 days.
Primary seed liquid fermentation: The *Antrodia camphorata* strain stored at 4° C. was activated, and the liquid seed medium was inoculated with a small square of 1 cm$^2$. Each bottle was filled with 80 mL of seed medium (250 mL), and after the inoculation, culture was carried out under the conditions of 28° C. and 110 r·min$^{-1}$ for 10 days.
Secondary shake flask liquid fermentation: The well-grown primary seed liquid was mixed, 500 mL shake flasks were uniformly inoculated with the mixed well-grown primary seed liquid, the amount of each bottle being 150 mL, and the inoculum volume being 10 mL, and after the inoculation, culture was carried out under the conditions of 28° C. and 110 r·min$^{-1}$ for 15 days.

Figure 2:
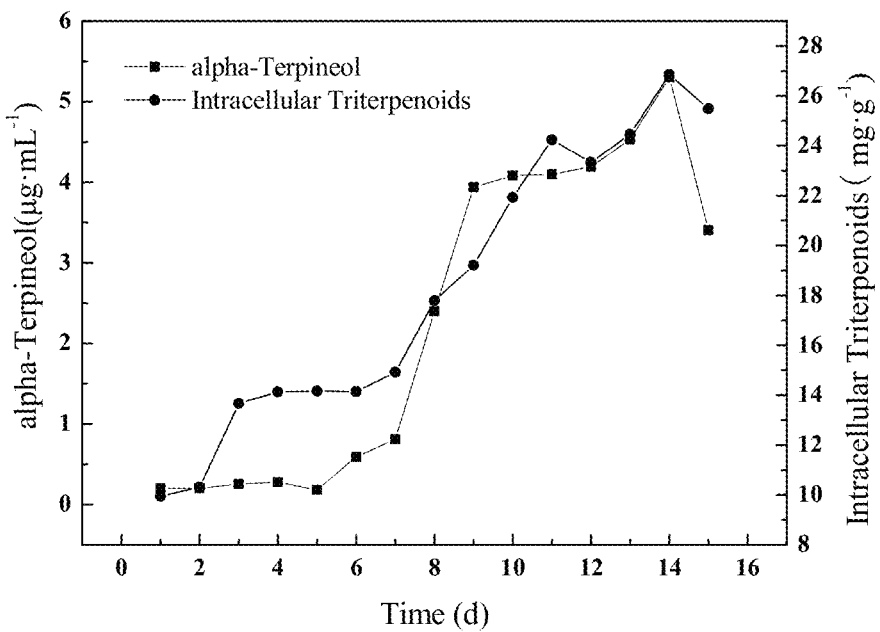
FIG. 2 shows the yields of α-terpineol and triterpenoids as a function of time in the fermentation process of Example 2.

(2) Off-Line Determination of Contents of α-Terpineol and Triterpenoids
Under the culture conditions of Example 2, the variation trend of contents of the α-terpineol and triterpenoids in the fermentation process are shown in FIG. 2. The variation trends of the two are consistent. Correlation analysis and unary linear regression analysis of α-terpineol and triterpenoids under such culture conditions show that the α-terpineol is positively correlated with triterpenoids in terms of content and the Pearson correlation coefficient is 0.942. Further, unary linear regression analysis was performed on the two to obtain the quantitative regression equation between the two as Y=2.721X+12.057.

The determination of the α-terpineol is the same as in Example 1.

EXAMPLE 3

(1) Culture Conditions 3
*Antrodia camphorata* strain: JMA 01, preserved by KYORI IND (SHENZHEN) Co. Ltd., Shenzhen.
PDA slant medium (g·L$^{-1}$): Potato 200, glucose 20, agar 20.
Seed liquid medium (g·L$^{-1}$): Bran 2.0, glucose 20, peptone 10, MgSO$_4$ 1.5, VB$_1$ 0.1, KH$_2$PO$_4$ 3.
Fermentation liquid medium (g·L$^{-1}$): Bran 2.0, glucose 20, peptone 10, MgSO$_4$ 1.5, VB$_1$ 0.1, KH$_2$PO$_4$ 3.

Seed slant: The *Antrodia camphorata* strain stored at 4° C. was activated, the PDA slant medium was inoculated with the activated *Antrodia camphorata* strain, and the activated *Antrodia camphorata* strain was cultured at 28° C. for 20 days.
Primary seed liquid fermentation: The *Antrodia camphorata* strain stored at 4° C. was activated, and the liquid seed medium was inoculated with a small square of 1 cm$^2$. Each bottle was filled with 80 mL of seed medium (250 mL), and after the inoculation, culture was carried out under the conditions of 28° C. and 110 r·min$^{-1}$ for 10 days.
Secondary shake flask liquid fermentation: The well-grown primary seed liquid was mixed, 500 mL shake flasks were uniformly inoculated with the mixed well-grown primary seed liquid, the amount of each bottle being 150 mL, and the inoculum volume being 10 mL, and after the inoculation, culture was carried out under the conditions of 28° C. and 110 r·min$^{-1}$ for 15 days.

Figure 3:
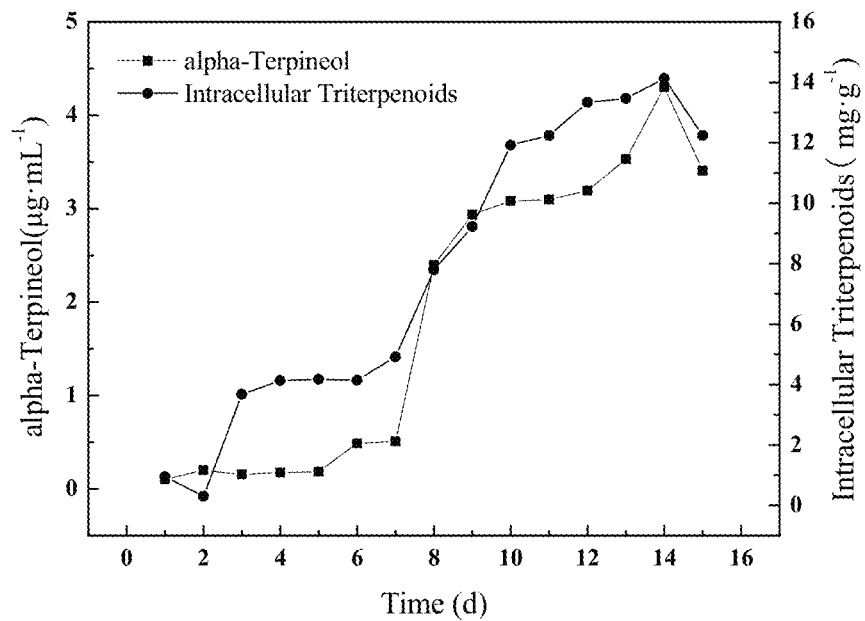
FIG. 3 shows the yields of α-terpineol and triterpenoids as a function of time in the fermentation process of Example 3.

(2) Off-Line Determination of Contents of α-Terpineol and Triterpenoids
Under the culture conditions of Example 3, the variation trend of contents of the α-terpineol and triterpenoids in the fermentation process are shown in FIG. 3. The variation trends of the two are consistent. Correlation analysis and unary linear regression analysis of α-terpineol and triterpenoids under such culture conditions show that the α-terpineol is positively correlated with triterpenoids in terms of content and the Pearson correlation coefficient is 0.961. Further, unary linear regression analysis was performed on the two to obtain the quantitative regression equation between the two as Y=2.360X+2.927.

The determination of the α-terpineol is the same as in Example 1.

EXAMPLE 4

Figure 4:
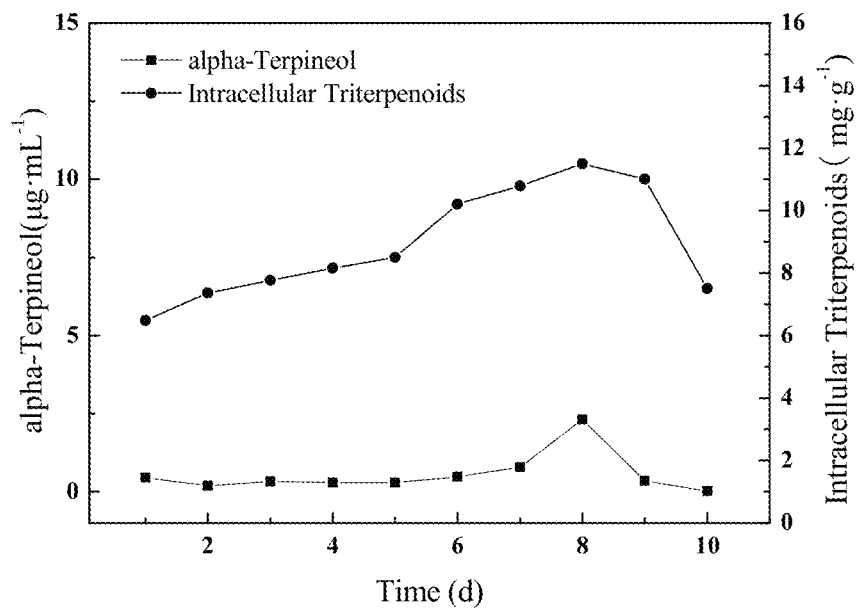
FIG. 4 shows the yields of α-terpineol and triterpenoids as a function of time in the fermentation process of Example 4.
Figure 5A:
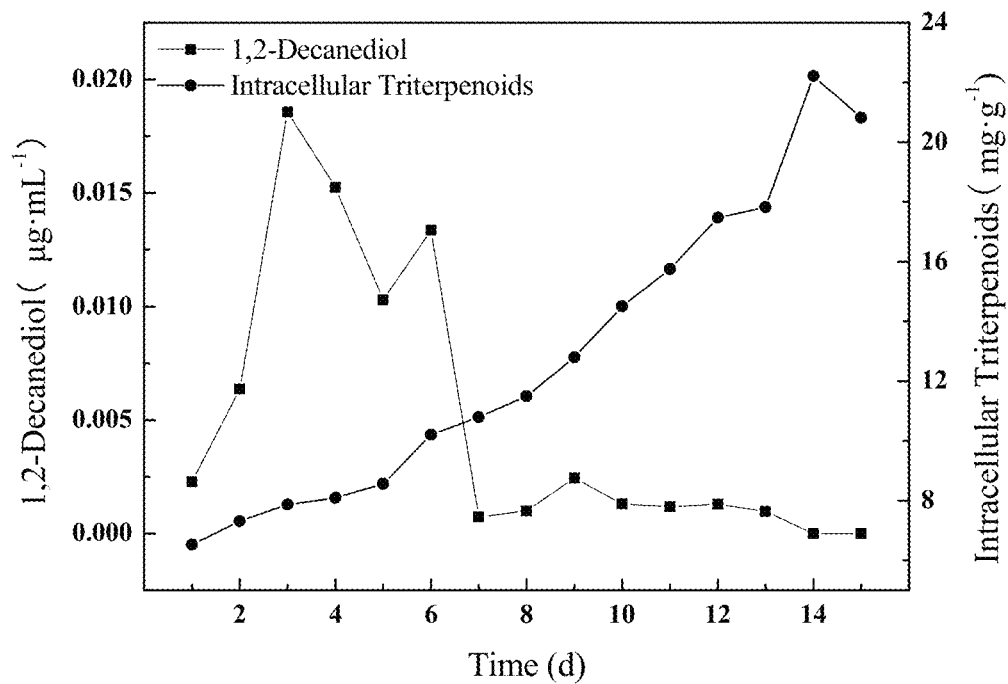
FIG. 5A-5J show the yields of other volatile substances and triterpenoids as a function of time in the fermentation process of Example 1.
Figure 5B:
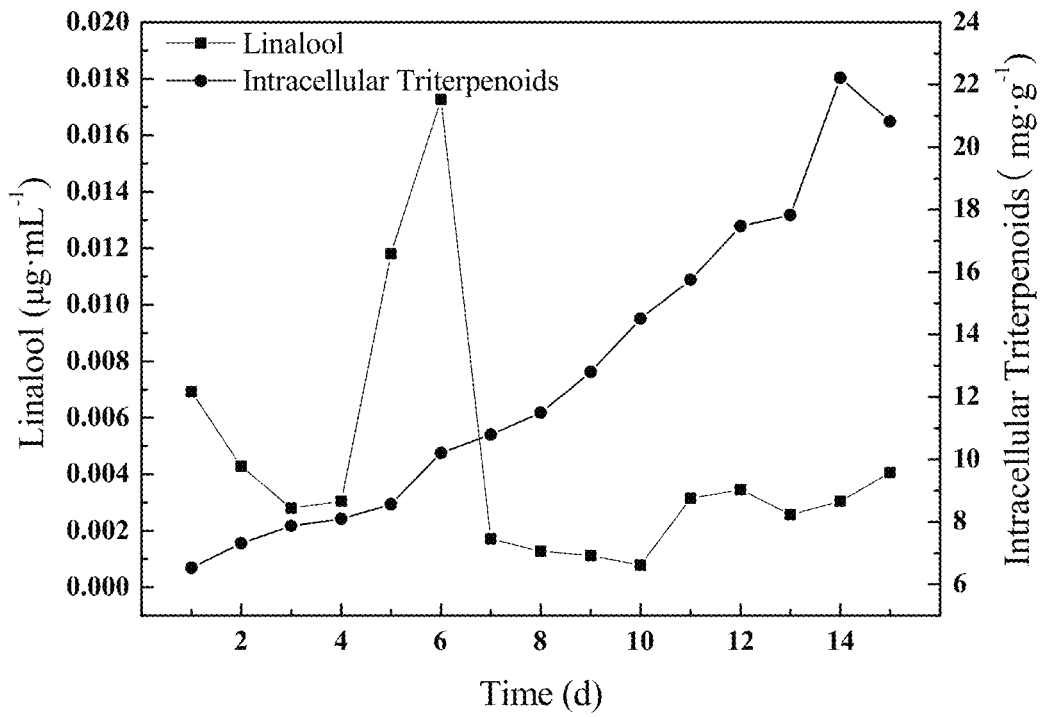
Figure 5C:
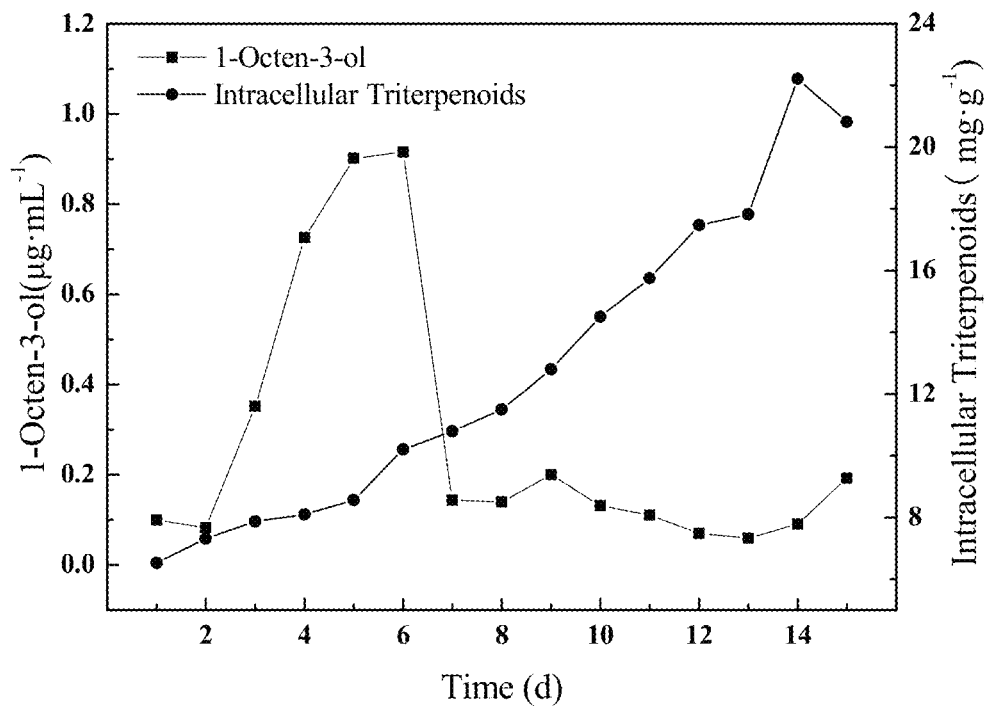
Figure 5D:
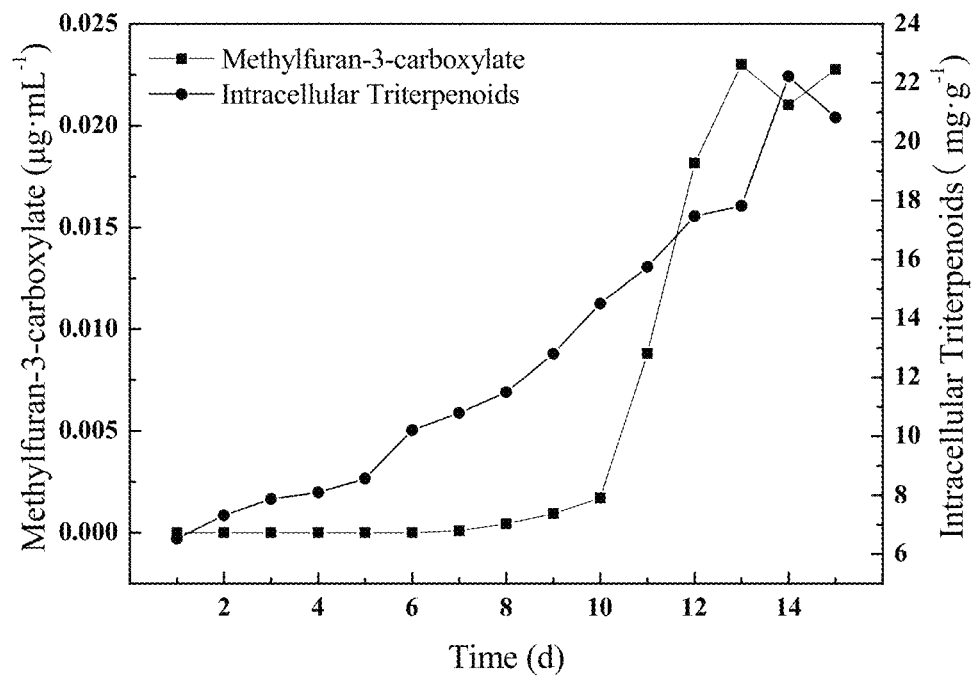
Figure 5E:
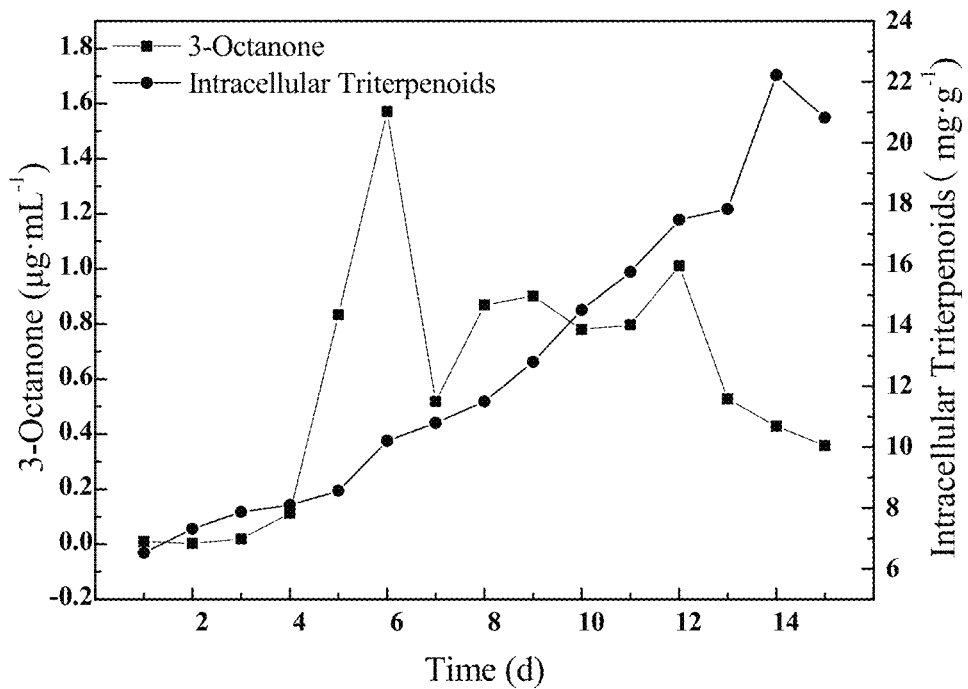
Figure 5F:
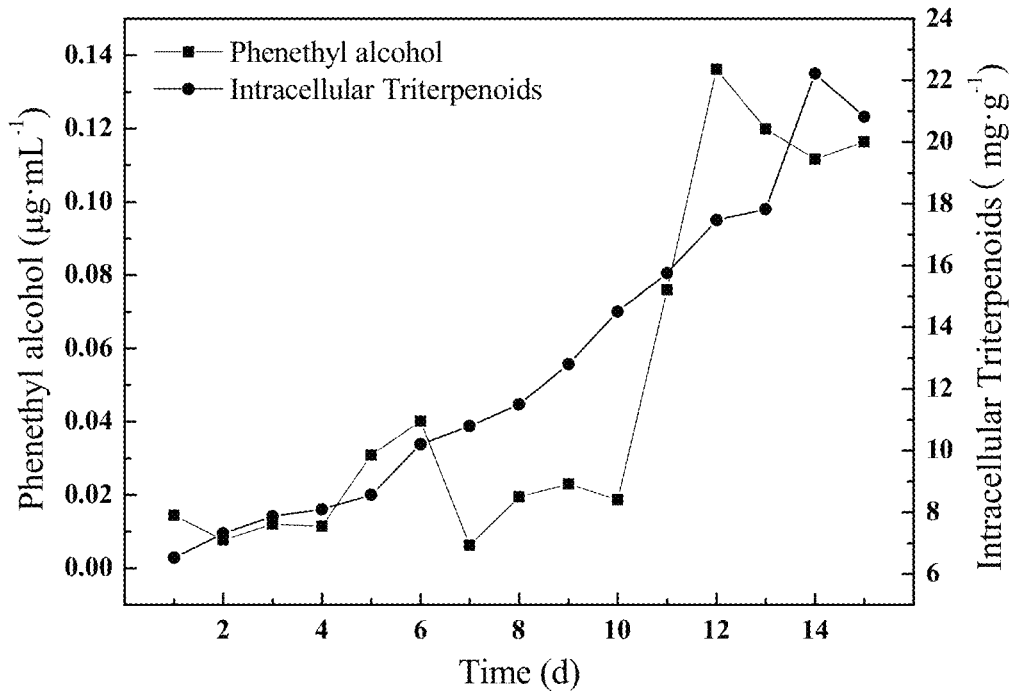
Figure 5G:
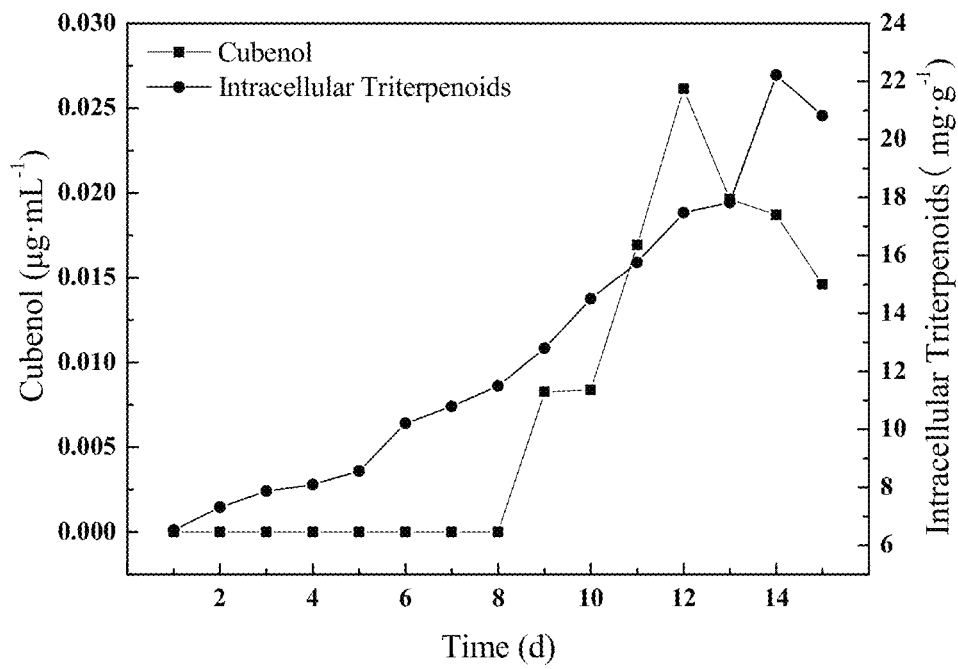
Figure 5H:
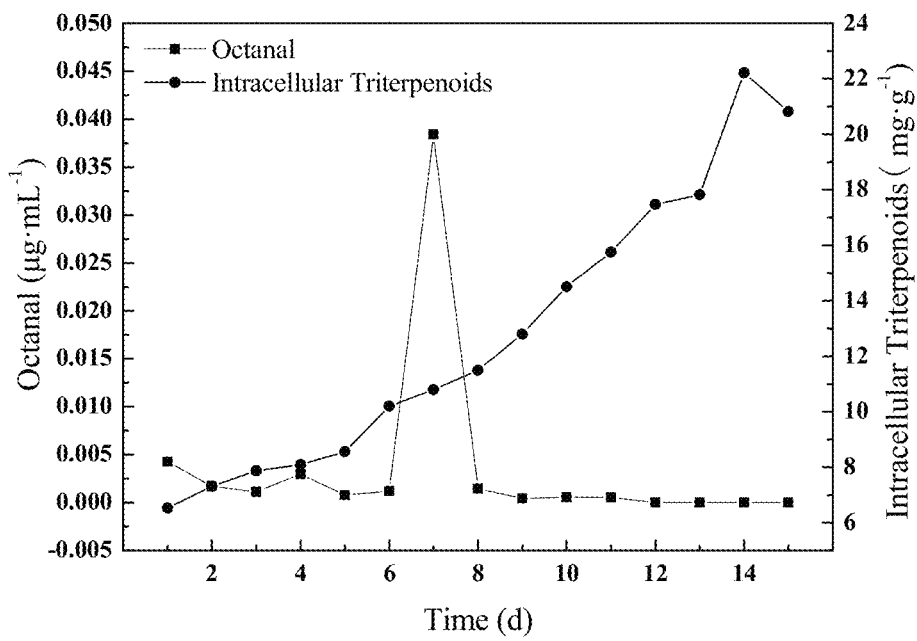
Figure 5I:
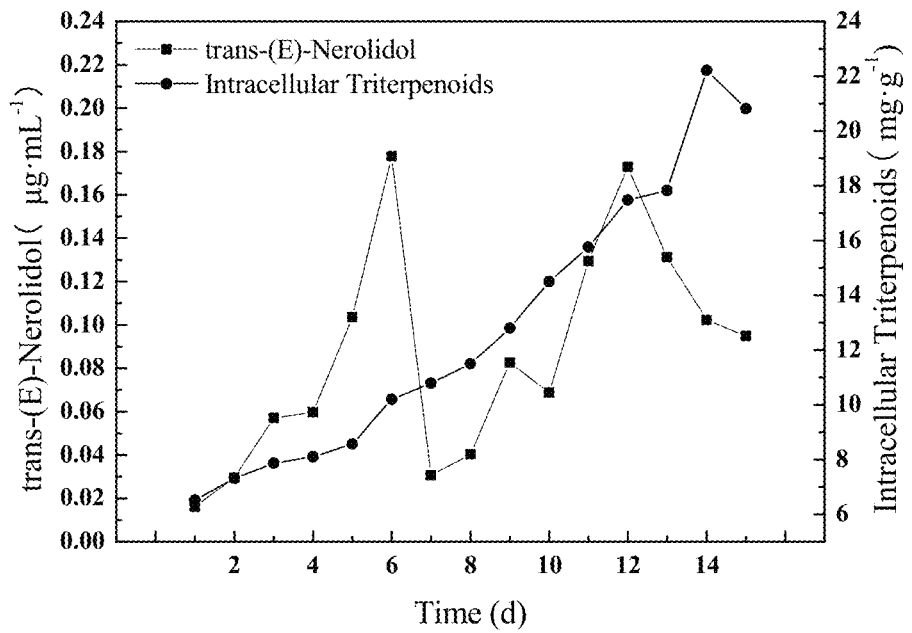
Figure 5J:
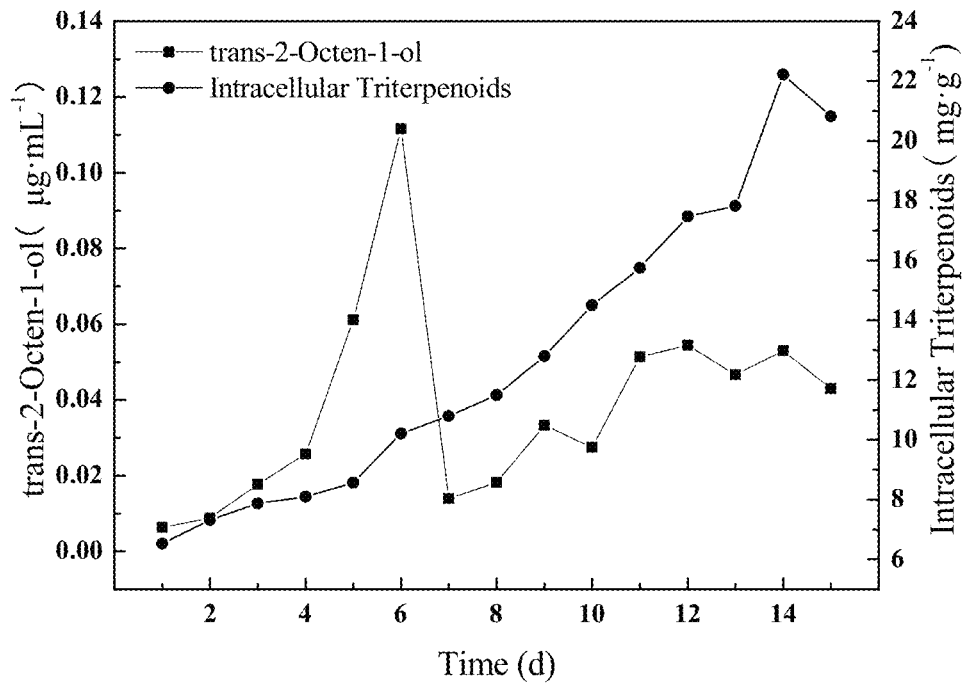
Figure 6A:
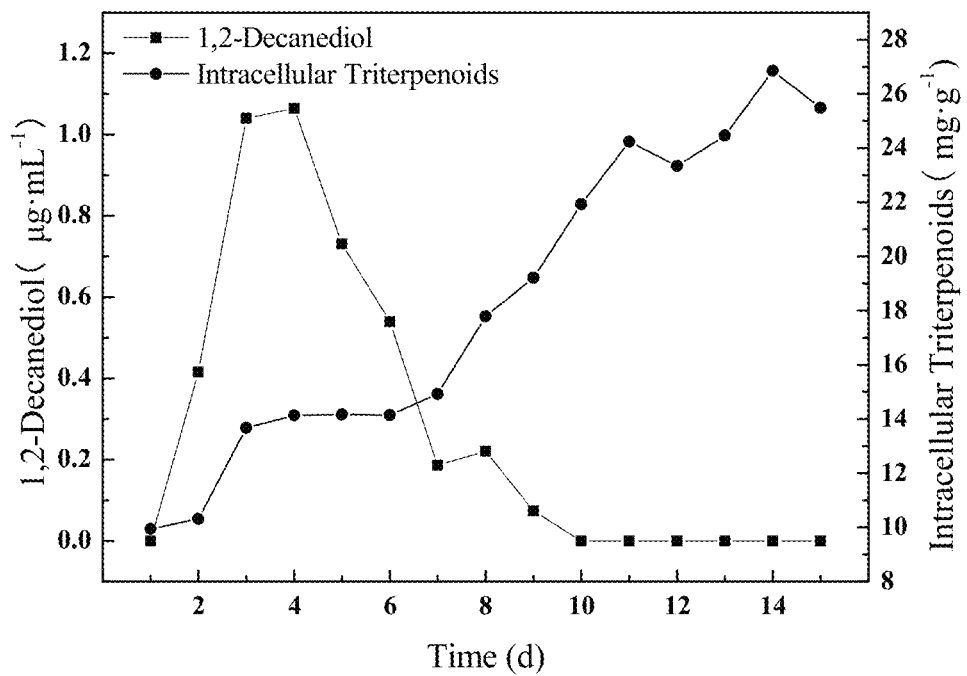
FIG. 6A-6J show the yields of other volatile substances and triterpenoids as a function of time in the fermentation process of Example 2.
Figure 6B:
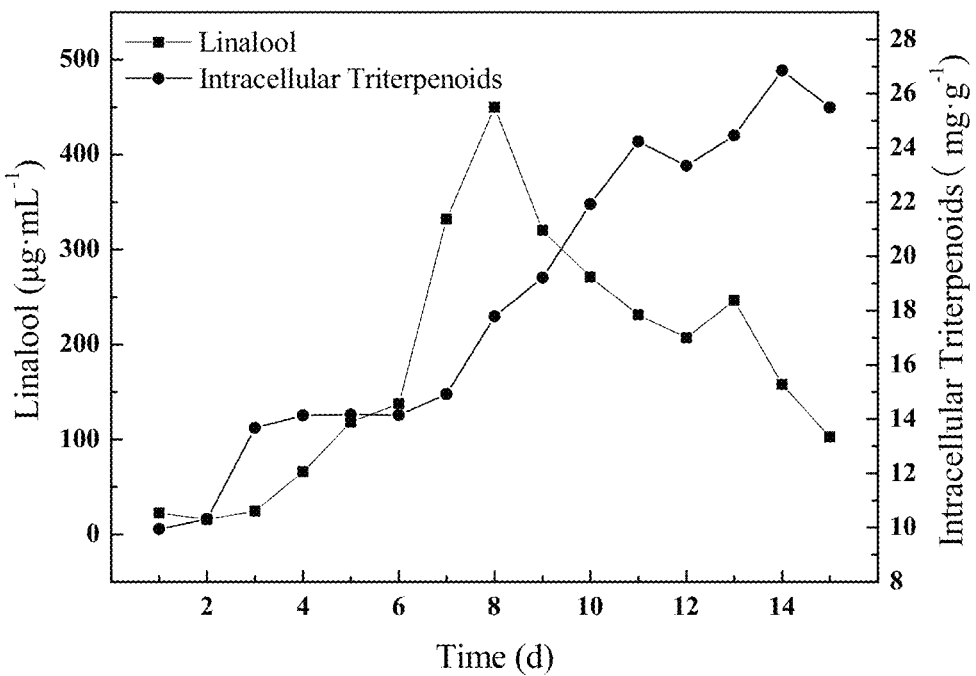
Figure 6C:
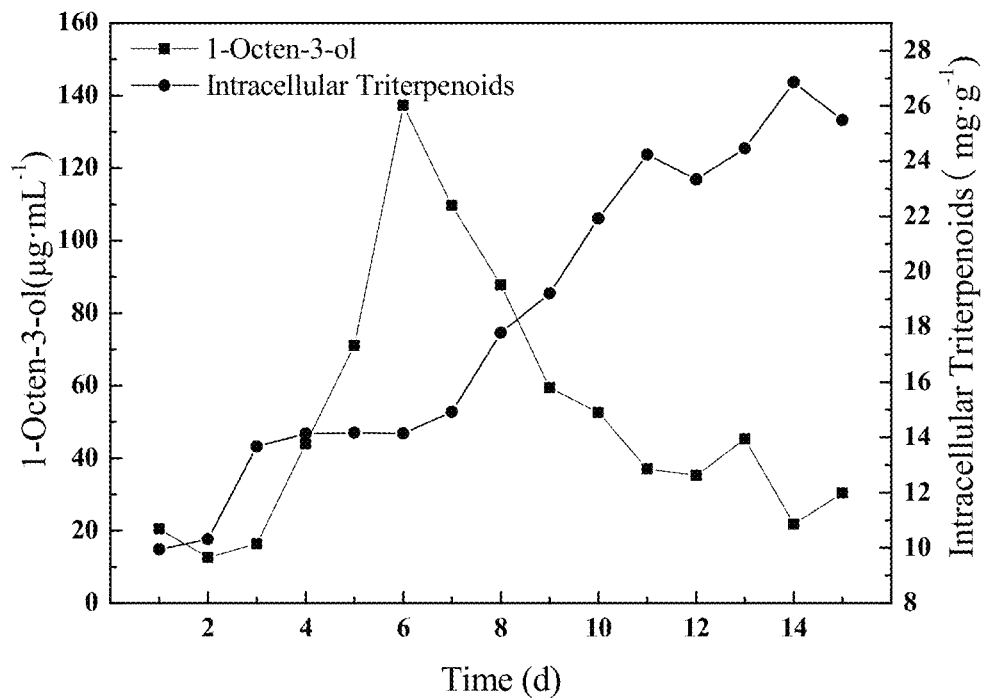
Figure 6D:
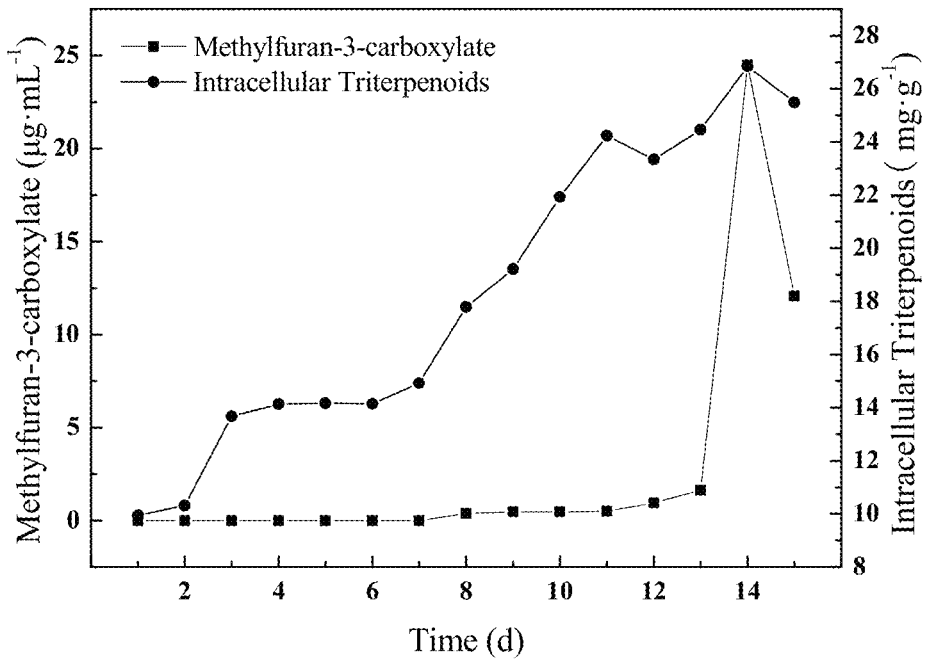
Figure 6E:
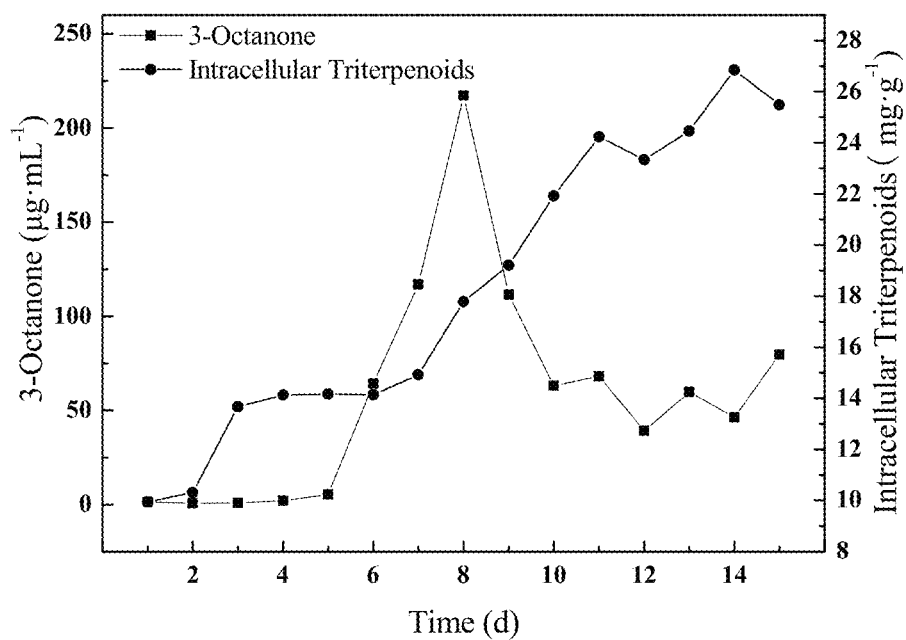
Figure 6F:
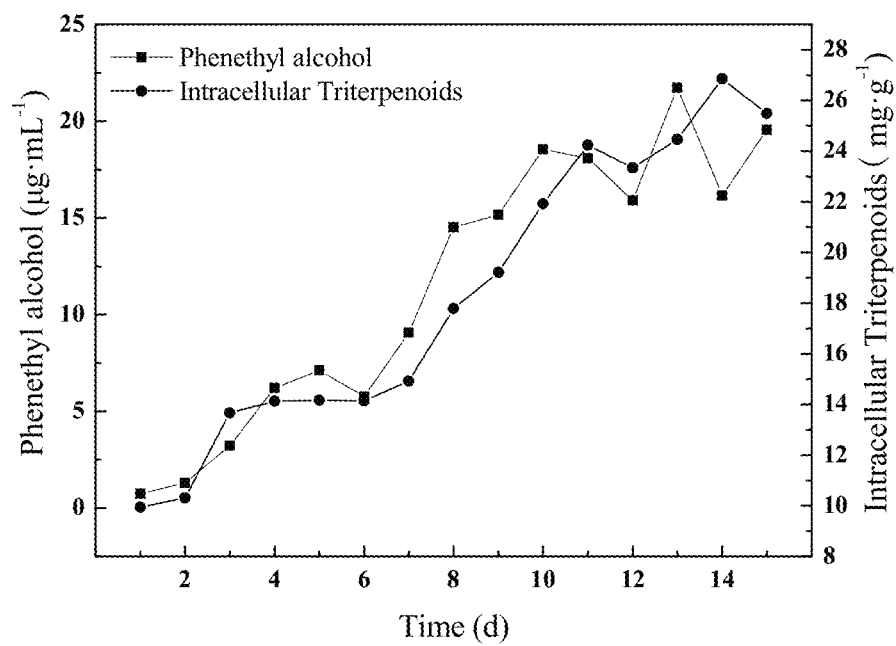
Figure 6G:
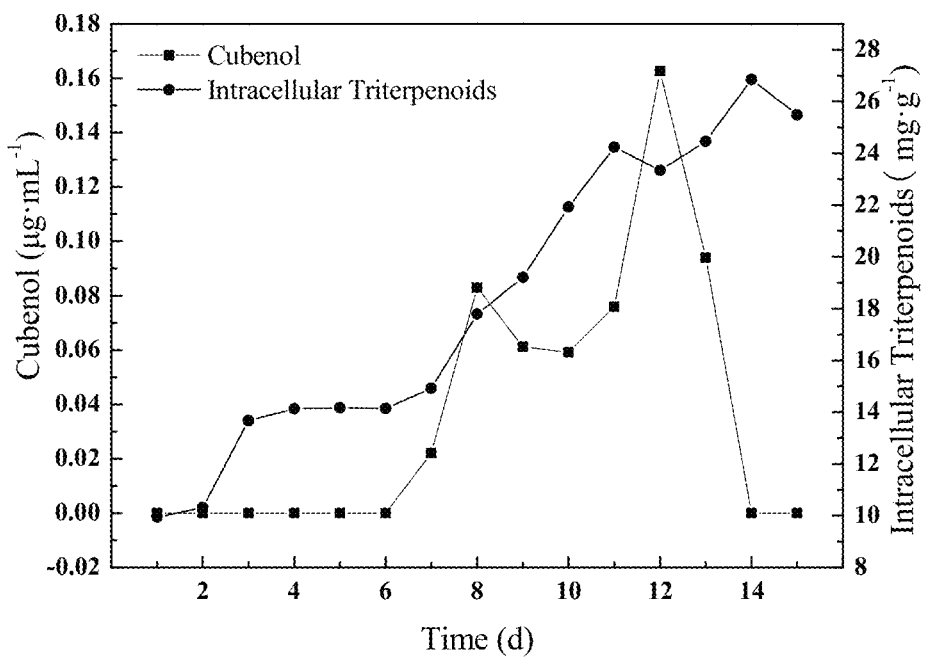
Figure 6H:
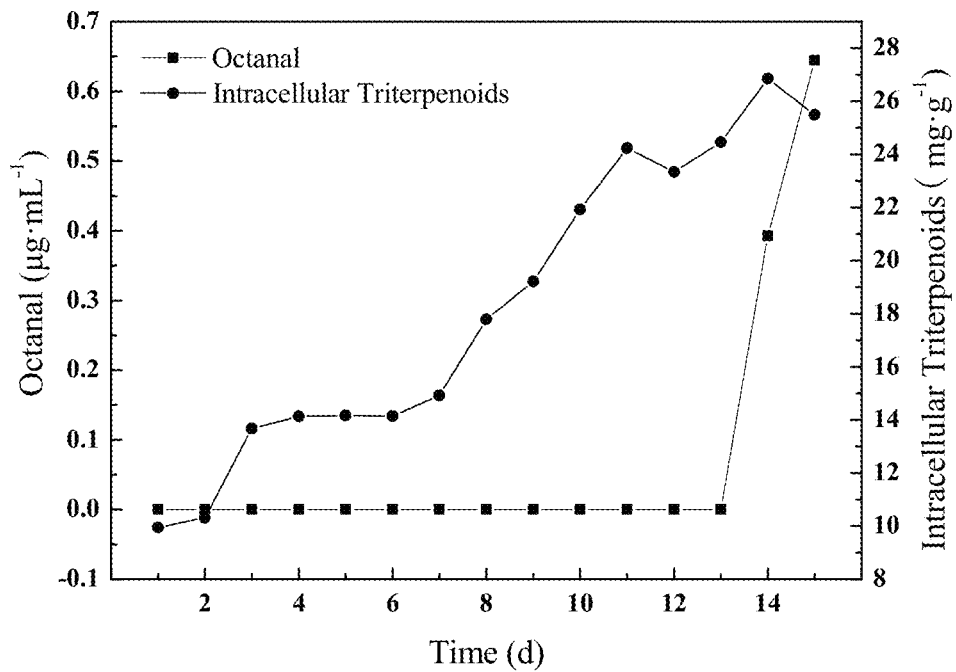
Figure 6I:
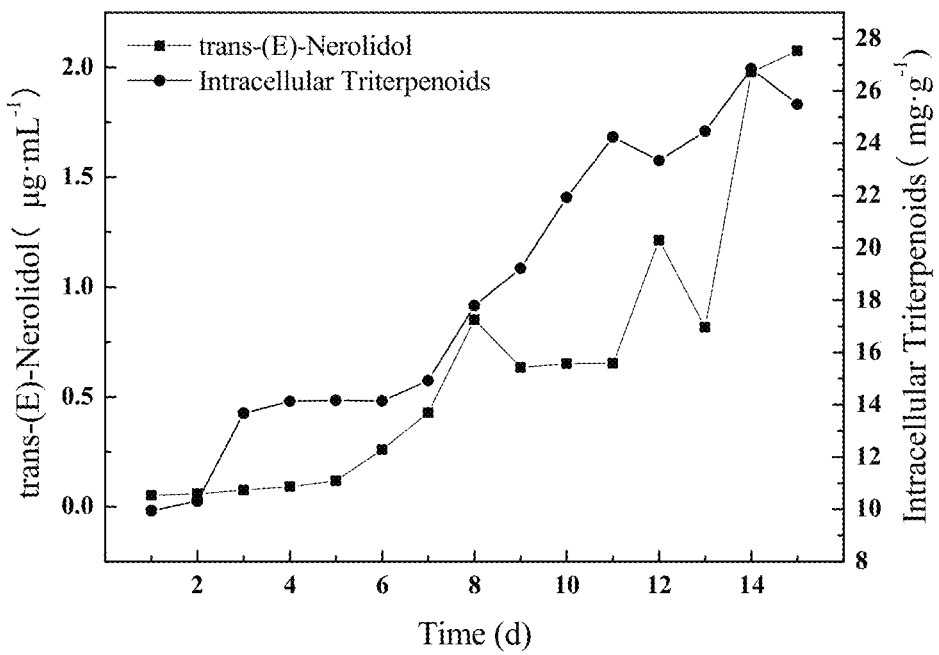
Figure 6J:
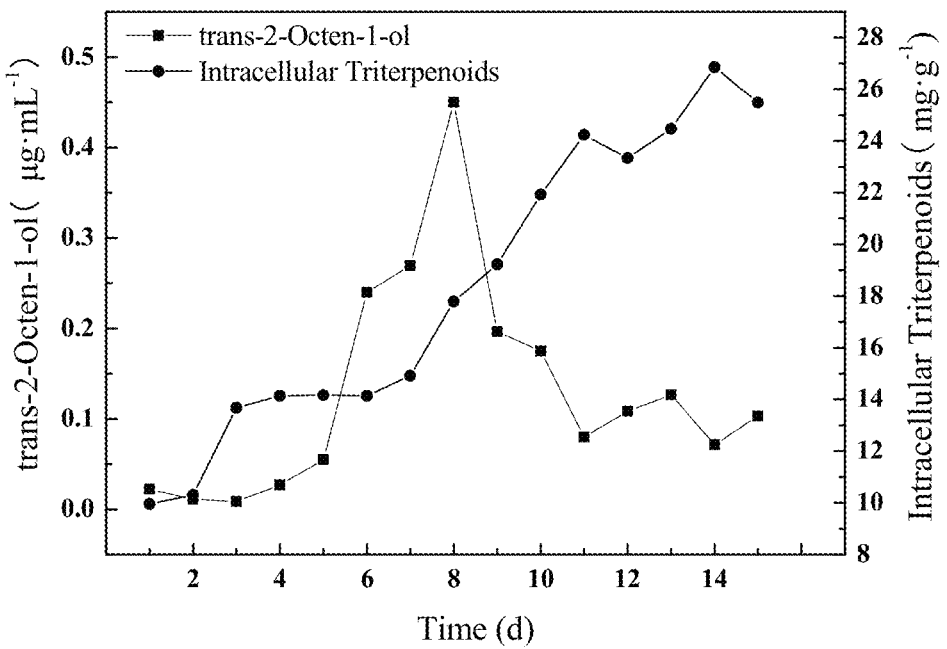

The conditions of implementation were the same as in Example 1. Compared to FIG. 1, the α-terpineol in FIG. 4 did not rise but fall after the 8$^{th}$ to 9$^{th}$ days, suggesting that the fermentation was abnormal. Microbiological contamination was found after sampling and microscopy, and the microbes causing contamination were bacteria. This indicates that the present invention can not only characterize the content variation of triterpenoids in the normal fermentation process, but also emit a prompt signal when the fermentation is abnormal.

COMPARATIVE EXAMPLE 1

Under the culture conditions of Example 1, the correlation analysis of other volatile compounds detected under the same conditions and triterpenoids was carried out, and the correlation coefficients were low, and were all lower than the correlation coefficient between α-terpineol and triterpenoids. The statistical analysis results are shown in Table 1.

Among them, the 1, 2-decanediol is negatively correlated with triterpenoids in terms of content, and the Pearson correlation coefficient is 0.630. The linalool is negatively correlated with triterpenoids in terms of content, and the correlation coefficient is 0.301. The 1-octen-3-ol is negatively correlated with triterpenoids in terms of content, and the Pearson correlation coefficient is 0.436. The methyl furan-3-carboxylate is positively correlated with triterpenoids in terms of content, and the Pearson correlation coefficient is 0.899. The 3-octanone is positively correlated with triterpenoids in terms of content, and the Pearson correlation coefficient is 0.233. The phenethyl alcohol is positively correlated with triterpenoids in terms of content, and the Pearson correlation coefficient is 0.869. The cubenol is positively correlated with triterpenoids in terms of content, and the Pearson correlation coefficient is 0.875. The n-caprylic octanal is negatively correlated with triterpenoids in terms of content, and the Pearson correlation coefficient is 0.202. The Trans-(E)-Nerolidol is positively correlated with triterpenoids in terms of content, and the Pearson correlation coefficient is 0.512. The trans-2-octen-1-ol is positively correlated with triterpenoids in terms of content, and the Pearson correlation coefficient is 0.326.

TABLE 1

Correlation analysis of other volatile substances and triterpenoids in the fermentation process of Example 1

| Volatile Substance | Pearson Correlation Coefficient | Volatile Substance | Pearson Correlation Coefficient |
|---|---|---|---|
| 1,2-decanediol | −0.630 | phenethyl alcohol | 0.869 |
| linalool | −0.301 | cubenol | 0.875 |
| 1-octen-3-ol | −0.436 | n-caprylic octanal | −0.202 |
| methyl furan-3-carboxylate | 0.899 | Trans-(E)-Nerolidol | 0.512 |
| 3-octanone | 0.233 | trans-2-octen-1-ol | 0.326 |

COMPARATIVE EXAMPLE 2

Under the culture conditions of Example 2, the correlation analysis of other volatile compounds detected under the same conditions and triterpenoids was carried out, and the Pearson correlation coefficients were low, and were all lower than the correlation coefficient between α-terpineol and triterpenoids. The statistical analysis results are shown in Table 2.

Among them, the 1, 2-decanediol is negatively correlated with triterpenoids in terms of content, and the Pearson correlation coefficient is 0.601. The linalool is positively correlated with triterpenoids in terms of content, and the correlation coefficient is 0.405. The 1-octen-3-ol is negatively correlated with triterpenoids in terms of content, and the Pearson correlation coefficient is 0.171. The methyl furan-3-carboxylate is positively correlated with triterpenoids in terms of content, and the Pearson correlation coefficient is 0.585. The 3-octanone is positively correlated with triterpenoids in terms of content, and the Pearson correlation coefficient is 0.306. The phenethyl alcohol is positively correlated with triterpenoids in terms of content, and the Pearson correlation coefficient is 0.809. The cubenol is positively correlated with triterpenoids in terms of content, and the Pearson correlation coefficient is 0.501. The n-caprylic Octanal is positively correlated with triterpenoids in terms of content, and the Pearson correlation coefficient is 0.530. The Trans-(E)-Nerolidol is positively correlated with triterpenoids in terms of content, and the Pearson correlation coefficient is 0.853. The trans-2-octen-1-ol is positively correlated with triterpenoids in terms of content, and the Pearson correlation coefficient is 0.120.

TABLE 2

Correlation analysis of other volatile substances and triterpenoids in the fermentation process of Example 2

| Volatile Substance | Pearson Correlation Coefficient | Volatile Substance | Pearson Correlation Coefficient |
|---|---|---|---|
| 1,2-decanediol | −0.601 | phenethyl alcohol | 0.809 |
| linalool | 0.405 | cubenol | 0.501 |
| 1-octen-3-ol | −0.171 | n-caprylic octanal | 0.530 |
| methyl furan-3-carboxylate | 0.585 | Trans-(E)-Nerolidol | 0.853 |
| 3-octanone | 0.306 | trans-2-octen-1-ol | 0.120 |

What is claimed is:

1. A method of rapid characterizing of production of triterpenoids in a liquid fermentation process of *Antrodia camphorate*, comprising:
   providing *Antrodia camphorate* in a liquid fermentation apparatus under fermentation conditions,
   quantitating the content of a volatile substance in the liquid fermentation process, wherein the volatile substance is α-terpineol,
   measuring a variation trend of the content of the volatile substance over time, and
   correlating triterpenoids production in the liquid fermentation process with the variation trend of the volatile substance, thereby determining the production of triterpenoids in the liquid fermentation process.

2. The method of claim 1, wherein the variation trend of content of the α-terpineol is consistent with a variation trend of content of triterpenoids.

3. The method of claims 1 wherein the content of α-terpineol is determined by an on-line detection of α-terpineol or an off-line detection of α-terpineol.

4. The method of claim 3, wherein the fermentation apparatus comprises a process mass spectrometer, an electronic nose, and other on-line detection instruments, and a parameter acquisition system.

5. The method of claim 4, wherein the method further comprises:
   detecting α-terpineol in an exhaust gas of the liquid fermentation apparatus,
   connecting an electronic nose through a hose to form a circulation loop to allow passage of the exhaust gas generated in the liquid fermentation process,
   monitoring the concentration of α-terpineol in the exhaust gas by the electronic nose, and
   calculating the amount of α-terpineol in a fermentation broth of the liquid fermentation.

6. The method of claim 3, wherein the off-line detection method further comprises:
   sampling a fermentation broth of the *Antrodia camphorate* fermentation liquid by a headspace solid phase microextraction-gas chromatography-mass spectrometer, and
   quantitating the α-terpineol in the sampled fermentation broth.

7. A method of quantifying triterpenoids produced in an *Antrodia camphorate* liquid fermentation process, which comprises:
   incubating *Antrodia camphorate* in a first fermentation broth under fermentation conditions,
   quantifying over time an amount of α-terpineol in the first fermentation broth,
   quantifying over time an amount of triterpenoids in the first fermentation broth, calculating a correlation between the amount of α-terpineol in the first fermentation broth and the amount of triterpenoids in the first fermentation broth, such that for any given amount of α-terpineol in the fermentation broth at any time in fermentation the amount of triterpenoids is known under the fermentation conditions without directly quantifying the triterpenoids in the fermentation process, fermenting *Antrodia camphorate* in a second fermentation broth under the fermentation conditions, and quantifying the amount of α-terpineol in the second fermentation broth, determining the amount of triterpenoids in the second fermentation broth based on the correlation and based on the amount of α-terpineol detected in the second fermentation broth, and wherein the first fermentation broth is the same as the second fermentation broth.

8. The method of claim 7, wherein determining the amount of triterpenoids in the second fermentation broth does not require directly assaying for triterpenoids and does not require the steps of: (1) solid-liquid separation, (2) room-temperature leaching, decoction, or heat reflux extraction on mycelium with organic solvents, and/or (3) direct assay determination of triterpenoids in the extraction.

9. The method of claim 7, wherein quantifying the amount of α-terpineol comprises obtaining a sample of exhaust gas from the second fermentation broth, and quantifying α-terpineol in the exhaust gas.

10. The method of claim 7, wherein quantifying the amount of α-terpineol occurs in real time.

11. The method of claim 7, wherein the first fermentation broth comprises bran, glucose, $MgSO_4 \cdot 7H_2O$, and $KH_2PO_4$, at pH 5.5.

12. The method of claim 7, wherein the correlation between the amount of α-terpineol in the first fermentation broth and the amount of triterpenoids in the first fermentation broth is a Pearson correlation coefficient of at least 0.9.

13. The method of claim 12, wherein the amount of α-terpineol in the first or second fermentation broth is determined by solid phase microextraction-gas chromatography-mass spectrometry of a centrifuged sample of the first or second fermentation broth.

\* \* \* \* \*